United States Patent [19]

Lehmussaari et al.

[11] Patent Number: 4,675,296

[45] Date of Patent: Jun. 23, 1987

[54] PROCESS FOR THE EXTRACTION OF β-AMYLASE FROM BARLEY GRAINS

[75] Inventors: Antti Lehmussaari; Aino Mansikkamaki, both of Jokioinen, Finland

[73] Assignee: Suomen Sokeri Oy, Finland

[21] Appl. No.: 618,600

[22] Filed: Jun. 8, 1984

Related U.S. Application Data

[63] Continuation-in-part of Ser. No. 340,531, Jan. 18, 1982, abandoned.

[51] Int. Cl.$^4$ .................... C12N 9/96; C12N 9/26; A23L 1/202
[52] U.S. Cl. .................... 435/188; 435/201; 435/185
[58] Field of Search ............ 435/95, 185, 201, 188; 426/28

[56] References Cited

U.S. PATENT DOCUMENTS

| | | | |
|---|---|---|---|
| 3,067,067 | 12/1962 | Etheridge et al. | 127/71 |
| 3,293,143 | 12/1966 | Heinicke | 435/188 |
| 3,492,203 | 1/1970 | Mitsuhashi et al. | 435/95 |
| 4,024,000 | 5/1977 | Shibata et al. | 435/201 X |

FOREIGN PATENT DOCUMENTS 0086861  8/1983  European Pat. Off. ........... 435/201

OTHER PUBLICATIONS

D. E. Briggs, *Barley*, Chapman & Hall, 1978, pp. VII–XI, 100, 101, 179, 180, 213.
A. H. Cook, *Barley and Malt*, Academic Press, 1962, pp. XI–XIV, 320, 321, 355, 412, 483, 585, 589–595, 597, 599.
J. R. A. Pollock, *Brewing Science*, Academic Press, 1979, pp. 34–37, 164, 261 and 262.
*Food Science and Technology Abstracts*, vol. 7, No. 1, 1975, 1 T 46.

*Primary Examiner*—Lionel M. Shapiro
*Attorney, Agent, or Firm*—Bernard, Rothwell & Brown

[57] ABSTRACT

The present invention comprises a method for preparing a commercial β-amylase product from whole or at least partially dehusked barley grain by extracting the grain with water. The water may optionally contain a reducing agent. The invention further comprises the purification, concentration and stabilization of the β-amylase solution and the resultant commerical product.

14 Claims, No Drawings

PROCESS FOR THE EXTRACTION OF β-AMYLASE FROM BARLEY GRAINS

CROSS REFERENCE

This application is a continuation-in-part of U.S. patent application Ser. No. 340,531, filed Jan. 18, 1982, now abandoned.

BACKGROUND OF THE INVENTION

Enzymes which are capable of hydrolyzing a preheated starch slurry include α-amylase, β-amylase, glucoamylase and α-1,6-glucosidases, pullulanase and isoamylase.

Starch is composed of amylose- and amylopectin molecules. Amylose is a straight chain of numerous glucose units which are connected to each other with α-1,4-glucosidic linkages. Amylopectin is a branched molecule where at the branchpoints the glucose chains are attached to each other with an α-1,6-linkage.

α-Amylase cuts α-1,4-linkages randomly from any part of the starch molecule yielding glucose chain residues of different shapes and sizes. β-Amylase acts differently—it yields maltose molecules (diglucose units) from the non-reducing ends of a starch molecule as long as it reaches a branchpoint which it cannot pass. Glucoamylase is capable of cutting both α-1,4- and α-1,6-linkages apart from certain very low molecular weight residues (2-4 glucose units which often have a branch point in the molecule), thus it yields glucose almost exclusively. Pullulanase and isoamylase cut only α-1,6-linkages.

For the liquifaction and saccharification of starch-containing slurries, as for example in brewing, distillation, and starch syrup manufacture, there are readily available various microbially produced commercial preparations such as α-amylase, glucoamylase and, also to some extent, pullulanase. (See, for example, Johnson, 1977, *Industrial Enzymes-Recent Advances*, Noyes Data Corp., New Jersey; Fogarty, 1983, *Microbial Enzymes and Biotechnology*, Applied Science Publishers, London and New York; and Godfrey & Reichelt, 1983, *Industrial Enzymology, The Applications of Enzymes in Industry*, Macmillan Publishers Ltd., The Nature Press, New York.)

There are also maltose-producing enzymes available. One is a so-called fungal-amylase which acts primarily like β-amylase but also partly like an α-amylase. The other is a so-called diastatic malt extract made from malted, i.e. germinated, barley. In addition to β-amylase, diastatic malt extract also contains substantial amounts of α-amylase and proteases.

All the above-mentioned preparations are enzyme mixtures. For several industrial users, however, a pure β-amylase is more suitable. According to present knowledge, pure β-amylase cannot be produced by microbes. β-Amylase is known, however, to be present in several crop plants including barley, wheat, soybeans and sweet potatoes. Best known is barley β-amylase, due to its importance in brewing. (See, for example, Cook, 1962, *Barley and Malt*, Academic Press, New York and London; Briggs, 1978, *Barley*, Chapman & Hall, London; Pollock, 1979, *Brewing Science* Vol. 1, Academic Press; and Briggs, Hough, Stevens & Young, 1981, *Malting and Brewing Science*, Chapman & Hall.)

A special application for pure β-amylase is the production of high maltose syrups having a very low glucose content. Such syrups offer distinct advantages in certain applications, for example, in confectionary applications.

The above-cited literature, its references and U.S. Pat. No. 3,492,203 disclose a plurality of methods for the separation of β-amylase from cultivated plants or components thereof. A common feature of all these methods is that the starting material is initially ground or crushed, or that it comprises some mechanically separated component of grain, such as wheat bran. From these starting materials, β-amylase is extracted with water, a buffer solution or the like. The obtained raw extract contains, together with β-amylase, a number of other soluble grain ingredients, which must be removed. This leads to very arduous purification and concentration steps in the enzyme preparation.

SUMMARY OF THE INVENTION

The invention provides for a process for extracting β-amylase which comprises steeping whole or at least partially dehusked barley grain in water at a temperature of from about 5° C. to about 50° C. for a period of from about 5 to about 70 hours to obtain an extract of β-amylase, wherein the grain surface layers act as a semipermeable filter, thereby allowing the enzyme to pass into the water, but retaining other grain ingredients.

BEST MODE FOR CARRYING OUT THE INVENTION

In accordance with the present invention, it has been found that β-amylase can be extracted by water from whole or at least partially dehusked barley grain without any prior crushing or grinding of the grain. The extracted enzyme is almost pure β-amylase. In the invention, the grain surface layers act as a semipermeable filter, allowing the enzyme and some low molecular weight substances to pass into the water. Most other components, however, are retained in the grain. Thus, the extract contains only minor amounts of impurities and is easily clarified and concentrated to a stable enzyme preparation. Extraction temperatures may range from about 5° C. to about 50° C., while extraction times may vary from about 5 to about 70 hours.

As is known from the literature, less than half of the grain's β-amylase is in free, readily available form, the rest being bound in grain proteins or other constituents. To get most of the β-amylase out of the grain, it is advisable before or during the steeping to convert the bound β-amylase to a free, active and extractable form. According to this invention, this is accomplished by the addition of reducing agents to the steeping liquor. Preferably, the reducing agents are sulfur-containing compounds which include sulfur dioxide and sulfurous acid or its salts. The concentration of the reducing agent preferably ranges from about 1 to 15 grams per liter (g/l). Those skilled in the art can readily ascertain the proper amount of reducing agent within this range for a particular extraction.

Examples 1 and 2 illustrate the extractability of β-amylase from different barley and wheat materials i.e. from whole barley, whole barley flours (dehusked 10%–15% of the grain's weight), barley and barley bran, whole wheat, whole wheat flour and wheat bran. The main characteristics tested were the speed of extraction in two temperatures, the ease of separation of raw extract from the grain material, the β-amylase yield from the raw extract and the purity of the raw extract, especially in relation to the content of soluble and insoluble impurities and their effect on the downstream purification and concentration steps. As can be seen from the results, 35% of the extractable β-amylase can be obtained from dehusked barley grains when the grains are steeped 24 hours at 20°–40° C. in an $SO_2$-containing steep water. The steep water, with its β-amylase, can be easily separated as a reasonably clear liquid from the grain by a single, one-stage mechanical sieving. The grain can thereafter be used for other purposes, such as the manufacture of barley syrup or barley starch. This simple separation process is in contrast to the complicated process needed to separate steep water from milled grain of bran. Multistage sieving and filtration is necessary in order to obtain a reasonably pure enzyme. The removal of suspended impurities is time consuming and expensive, while valuable components from the raw material are lost in the wastes.

The dilute β-amylase solution which is obtained according to the present invention is easily clarified by pre-coat filtration using, for example, diatomaceous earth as a filter aid. The residual grain from which the enzyme has been extracted still contains its original amount of starch, fiber and other valuable ingredients. The further concentration (and purification) of the β-amylase can be carried out using any well-known technique used in commercial enzyme manufacture, for example, precipitation with salt or organic solvent, ultrafiltration, dialysis, reverse osmosis, vacuum evaporation, freeze drying, etc. Ultrafiltration is the preferred method.

The purified and concentrated solution as such is very seldom a stable product. The enzyme activity deteriorates either because of chemical or microbiological reasons. The same applies to the barley β-amylase preparation obtained according to the prescribed procedure. This can be seen from the results shown in Example 3.

Stabilization of the β-amylase can be carried out by adding to the purified and concentrated β-amylase preparation suitable amounts of materials and additives which increase the dry, soluble solids content and osmotic pressure of the liquid together with suitable amounts of antimicrobial agents approved in enzyme preparations. These substances can be sugars, salts, acids, sugar alcohols or other products containing small molecules. Examples include such sugar-containing substances as molasses. Suitable acids include benzoic, sorbic and propionic acid, their salts and their esters.

The final commercial barley β-amylase preparation is a clear, dark, non-viscous liquid with defined and declared β-amylase activity (500°–4000°DP according to Food Chemicals Codex III-method, page 484). It is stabilized with substances raising its dry solids content and osmotic pressure and with approved antimicrobial agents. It keeps its activity (±15%) at 0°–10° C. for at least a year and at 20°–25° C. for at least three months. It contains no other hydrolytic activities, at least not in amounts of any significance.

Example 4 provides a comparison of the use of barley β-amylase, fungal amylase and diastatic malt extract, with and without the use of pullulanase, in the manufacture of maltose syrups. As can be seen, barley β-amylase is very competitive and applicable in the manufacture of maltose syrups, especially if low glucose contents are needed.

EXAMPLE 1

β-amylase was extracted separately from various barley and wheat materials at 20° C. using 10 g samples and 100 ml water. The water contained sufficient sulfur dioxide to convert bound β-amylase to an extractable form. Results are summarized in Table I.

EXAMPLE 2

β-Amylase was extracted from dehusked barley, barley flour and wheat bran at 40° C. using 10 g samples and the $SO_2$-water mixture of Example 1. Results are summarized in Table II.

EXAMPLE 3

The stability of concentrated barley β-amylase at 20° C. was measured before and after the addition of stabilizers. Results are given in Table III.

EXAMPLE 4

Maltogenic enzymes were used in the manufacture of maltose syrups. The substrate was 35 percent DS enzymatically liquified maltodextrin DEM. Saccharification time was 48 hours at 57° C., pH 6.0. Results are sumarized in Table IV.

TABLE I

| | Barley flour | | Wheat flour | | Wheat bran | | Barley bran | | Dehusked barley | | Whole barley | | Whole wheat | |
|---|---|---|---|---|---|---|---|---|---|---|---|---|---|---|
| Steeping time (hours) | 5 | 24 | 5 | 24 | 5 | 24 | 5 | 24 | 5 | 24 | 5 | 24 | 5 | 24 |
| Extract yield, ml | 72 | 73 | 70 | 71 | 54 | 47 | 53 | 52 | 87 | 85 | 89 | 85 | 89 | 88 |
| Filtration time, minutes (by gravity through a MN 640 folded paper) | 9 | 9 | 75 | 80 | 25 | 65 | 13 | 13 | 1.5 | 2 | 1 | 2 | 1 | 1.5 |
| Turbidity of extract | Slight | Slight | Moderate | Moderate | High | High | High | High | Slight | Slight | Clear | Clear | Clear | Clear |
| Beta-amylase activity in extract °DP/ml | 12.4 | 13.8 | 6.0 | 6.9 | 6.8 | 7.4 | 5.0 | 5.7 | 1.6 | 4.3 | 0.2 | 0.3 | 0.05 | 0.1 |
| Beta-amylase yield °DP/gram material | 89.3 | 102.2 | 41.4 | 48.6 | 31.4 | 34.5 | 25.7 | 28.1 | 14.0 | 35.8 | 1.8 | 2.5 | 0.4 | 0.9 |
| Beta-amylase yield (in percent of barley flour) | | 100 | | 47.5 | | 33.8 | | 27.5 | | 35.0 | | 2.5 | | 0.9 |
| Purity of extract °DP/grain extract dry substance | 970 | 1000 | 420 | 490 | 260 | 290 | 280 | 330 | 240 | 430 | 40 | 70 | 10 | 20 |
| Specific activity | 5630 | 5700 | 2150 | 2340 | 1080 | 1150 | 1400 | 1490 | 3860 | 5300 | protein | | protein | |

TABLE I-continued

|  | Barley flour | Wheat flour | Wheat bran | Barley bran | Dehusked barley | Whole barley | Whole wheat |
|---|---|---|---|---|---|---|---|
| °DP/gram extract protein |  |  |  |  |  | below detection limit | below detection limit |

TABLE II

|  | Barley flour |  | Wheat bran |  | Dehusked barley |  |
|---|---|---|---|---|---|---|
| Steeping time (h) | 24 | 48 | 24 | 48* | 24 | 48 |
| Extract yield, ml | 75 | 72 | 44 |  | 89 | 83 |
| Filtration time, minutes (by gravity through a MN 640 folded paper) | 12 | 12 | 22 |  | 1 | 3 |
| Turbidity of extract | moderate | moderate | High |  | slight | slight |
| Beta-amylase activity in extract °DP/ml | 14.6 | 13.0 | 10.2 |  | 4.3 | 8.0 |
| Beta-amylase yield °DP/gram material | 106.5 | 93.6 | 44.9 |  | 38.3 | 66.4 |
| Beta-amylase yield (in percent of barley flour) | 100 | 87.9 | 42.2 |  | 36.0 | 62.3 |
| Purity of extract °DP/grain extract dry substance | 950 | 800 | 390 |  | 745 | 1155 |
| Specific activity °DP/gram extract protein | 5010 | 4050 | 1620 |  | 8460 | 9750 |

*Sample destroyed

TABLE III

| | Unstabilized Sample | | | Stabilized Sample | | |
|---|---|---|---|---|---|---|
| Initial value | Activity °DP/ml | pH | Total Microbial Count, colonies/ml | Activity | pH | Total count |
|  | 1656 | 5.9 | 670 | 1656 | 5.9 | 670 |
| 2 weeks | 1472 | 5.9 | 170 × 10⁶ | 1656 | 5.9 | 270 |
| 1 month |  |  |  | 1656 | 5.9 | 260 |
| 2 months |  |  |  | 1656 | 5.9 | 260 |
| 3 months |  |  |  | 1564 | 5.9 | 130 |
| 6 months |  |  |  | 1449 | 5.9 | 20 |

TABLE IV

|  | Barley beta-amylase | | Fungal amylase (Novo Fungaryl 1660 S)[1] (7000° DP) | | Diastatic malt extract (ABM Diamalt 400° DP)[2] | |
|---|---|---|---|---|---|---|
| Maltogenic enzyme dosage °DP/kg DS | 300 | 1500 | 300 | 1500 | 300 | 1500 |
| Pullulanase Dosage 1/kg DS (ABM Pulluzyme 7502)[2] | — | 1.33 | — | 1.33 | — | 1.33 |
| Syrup composition %/DS |  |  |  |  |  |  |
| glucose | 1.2 | 1.3 | 2.1 | 4.3 | 1.7 | 2.5 |
| maltose | 53.9 | 65.4 | 24.1 | 46.0 | 55.5 | 68.4 |
| maltoriose | 13.2 | 15.7 | 27.5 | 27.2 | 15.1 | 20.4 |
| oligosaccharides | 31.7 | 17.6 | 46.3 | 22.4 | 27.7 | 8.7 |

Product supplied by:
[1] Novo Industri A/S, Denmark
[2] Associated British Maltsters, UK

We claim:

1. A process for extracting beta-amylase from barley, that has not been crushed or ground comprising: steeping whole or at least partially dehusked barley grain in water at a temperature of from about 5° C. to about 50° C. for a period of from about 5 to about 70 hours to obtain an extract of $\beta$-amylase, wherein the grain surface layers act as a semipermeable filter, thereby allowing the enzyme to pass into the water, but retaining other grain ingredients.

2. The process of claim 1, wherein a reducing agent is added to the steeping water to free $\beta$-amylase bound in grain proteins and other constituents of the barley.

3. The process of claim 2, wherein the reducing agent is sulfur dioxide, sulfurous acid or its salts and is present in an amount of between about 1 and about 15 grams per liter of steeping water.

4. The process of claim 3, wherein the process includes stabilizing the $\beta$-amylase extract with a substance selected from the group consisting of salts, sugars, sugar alcohols and acids.

5. The process of claim 4, wherein the stabilizing substance is selected from the group consisting of molasses, benzoic acid, sorbic acid, propionic acid and salts and esters of the acids.

6. The process of claim 5, wherein dehusked barley grain is extracted in steeping water having a concentration of sulfur dioxide sufficient to convert bound $\beta$-amylase in the grain to an extractable form.

7. The process of claim 6, wherein the extraction was carried out at about 20° C. for a period of about 24 hours.

8. A beta-amylase composition prepared according to the process of claim 1 and comprising β-amylase and a stabilizer, said composition being substantially free of other hydrolytic activities, having a β-amylase activity of 500°–4000°DP according to Food Chemical Codex-III method and being capable of maintaining its enzymatic activity (±15%) at 0°–10° C. for at least one year and at 20°–25° C. for at least three months.

9. A β-amylase composition prepared according the process of claim 2 and comprising β-amylase and a stabilizer, said composition being substantially free of other hydrolytic activities, having a β-amylase activity of 500°–4000°DP according to Food Chemical Codex-III method and being capable of maintaining its enzymatic activity (±15%) at 0°–10° C. for at least one year and at 20°–25° C. for at least three months.

10. A β-amylase composition prepared according to the process of claim 3 and comprising β-amylase and a stabilizer, said composition being substantially free of other hydrolytic activities, having a β-amylase activity of 500°–4000°DP according to Food Chemical Codex-III method and being capable of maintaining its enzymatic activity (±15%) at 0°–10° C. for at least one year and at 20°–25° C. for at least three months.

11. A β-amylase composition prepared according to the process of claim 4 and comprising beta-amylase and a stabilizer, said composition being substantially free of other hydrolytic activities, having a β-amylase activity of 500°–4000°DP according to Food Chemical Codex-III method and being capable of maintaining its enzymatic activity (±15%) at 0°–10° C. for at least one year and at 20°–25° C. for at least three months.

12. A beta-amylase composition prepared according to the process of claim 5.

13. A beta-amylase composition prepared according to the process of claim 6.

14. A beta-amylase composition prepared according to the process of claim 7.

* * * * *